(12) United States Patent
Walters

(10) Patent No.: US 7,776,041 B1
(45) Date of Patent: Aug. 17, 2010

(54) METHOD AND APPARATUS FOR IMPLANTING A SUTURE ANCHOR

(75) Inventor: Troy Walters, Plymouth, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 1277 days.

(21) Appl. No.: 10/889,623

(22) Filed: Jul. 12, 2004

(51) Int. Cl.
*A61F 5/00* (2006.01)
*A61F 2/00* (2006.01)
*A61B 17/58* (2006.01)
*A61B 17/60* (2006.01)

(52) U.S. Cl. .................... 606/86 R; 606/92
(58) Field of Classification Search ............. 606/92–99, 606/104, 72–73, 232, 139–142, 151, 86, 606/281, 213, 300
See application file for complete search history.

(56) References Cited

U.S. PATENT DOCUMENTS

| | | | | |
|---|---|---|---|---|
| 4,653,489 A | * | 3/1987 | Tronzo | 606/65 |
| 5,405,359 A | * | 4/1995 | Pierce | 606/232 |
| 5,417,691 A | * | 5/1995 | Hayhurst | 606/232 |
| 5,437,631 A | * | 8/1995 | Janzen | 604/506 |
| 5,549,633 A | * | 8/1996 | Evans et al. | 606/139 |
| 5,550,172 A | | 8/1996 | Regula et al. | |
| 5,618,314 A | | 4/1997 | Harwin et al. | |
| 5,649,959 A | * | 7/1997 | Hannam et al. | 606/213 |
| 5,679,723 A | | 10/1997 | Cooper et al. | |
| 5,871,484 A | | 2/1999 | Spievach et al. | |
| 5,925,051 A | * | 7/1999 | Mikhail | 606/94 |
| 6,048,343 A | | 4/2000 | Mathis et al. | |
| 6,165,203 A | | 12/2000 | Krebs | |
| 6,524,316 B1 | | 2/2003 | Nicholson et al. | |
| 6,610,079 B1 | * | 8/2003 | Li et al. | 606/232 |
| 6,620,185 B1 | * | 9/2003 | Harvie et al. | 606/232 |
| 2003/0077311 A1 | * | 4/2003 | Vyakarnam et al. | 424/426 |
| 2004/0225292 A1 | * | 11/2004 | Sasso et al. | 606/73 |

* cited by examiner

*Primary Examiner*—Julian W Woo
*Assistant Examiner*—Dianne Dornbusch
(74) *Attorney, Agent, or Firm*—Harness, Dickey

(57) ABSTRACT

An apparatus and method for delivering biologic material to a bone hole includes a delivery structure defining a proximal end and a distal end. The delivery structure includes a first longitudinal member defining a first cavity and extending between the distal and proximal end. A second longitudinal member is disposed around the first longitudinal member and extends between the distal and proximal end. The first and second longitudinal members define a second cavity therebetween. The first cavity is adapted to receive a flexible member therethrough. The second cavity is adapted to receive the biologic material and deliver the biologic material out of the distal end into the bone hole. The first longitudinal member precludes the biologic material from contacting the flexible member while the biologic material is delivered to the bone hole.

27 Claims, 3 Drawing Sheets

METHOD AND APPARATUS FOR IMPLANTING A SUTURE ANCHOR

FIELD OF THE INVENTION

The present invention relates to suture anchor implantation and more particularly to an assembly for delivering biologic material around a suture anchor implanted in a bone hole.

BACKGROUND OF THE INVENTION

It is often necessary to secure soft tissues, tendons and ligaments to bone during orthopedic surgical procedures in both human and animal patients. One way to attach soft tissue to a bone is to implant an anchor member into a hole formed in the bone. A suture strand is secured to the anchor member and, thus, is available for assisting in the attachment of soft tissues, tendons and ligaments to the bone.

Sometimes it is necessary to locate biologic material around the anchor member in the bone hole to enhance the holding ability of the anchor member in the bone hole. In doing so, it may be challenging to locate the biologic material into the bone hole while keeping the suture strand extending from the anchor member away from contact with the biologic material.

SUMMARY OF THE INVENTION

An apparatus for delivering biologic material to a bone hole includes a delivery structure defining a proximal end and a distal end. The delivery structure includes a first longitudinal member defining a first cavity and extending between the distal and proximal end. A second longitudinal member is disposed around the first longitudinal member and extends between the distal and proximal end. The first and second longitudinal members define a second cavity therebetween. The first cavity is adapted to receive a flexible member therethrough. The second cavity is adapted to receive the biologic material and deliver the biologic material out of the distal end into the bone hole. The first longitudinal member precludes the biologic material from contacting the flexible member while the biologic material is delivered to the bone hole.

According to other features, at least one support member extends between the first and second longitudinal members for maintaining the first and second longitudinal members in the offset relationship. The second longitudinal member defines a port for receiving the biologic material. A plunger is slidably disposed in the delivery structure and communicates with the second cavity. The plunger is operable to urge the biologic material toward the distal end and out of the distal end into the bone hole.

A method for implanting an anchor and delivering biologic material into a bone hole includes coupling a flexible member to an anchor. The anchor is positioned in the bone hole. A protective barrier is located relative to the flexible member. The biologic material is delivered around the bone hole wherein the protective barrier substantially precludes the biologic material from contacting the flexible member.

According to other features locating the protective barrier includes locating the flexible member through a first cavity defined by a first longitudinal member. The method further includes placing the biologic material into a second cavity defined between the first longitudinal member and a second longitudinal member. Placing the biologic material in the second cavity includes injecting the biologic material through a port defined on the second longitudinal member. Delivering the biologic material includes actuating a plunger slidably disposed within the second cavity toward the bone hole whereby the biologic material is forcibly expelled into the bone hole.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the embodiment(s) is merely exemplary in nature and is in no way intended to limit the invention, its application, or uses.

Figure 5A:
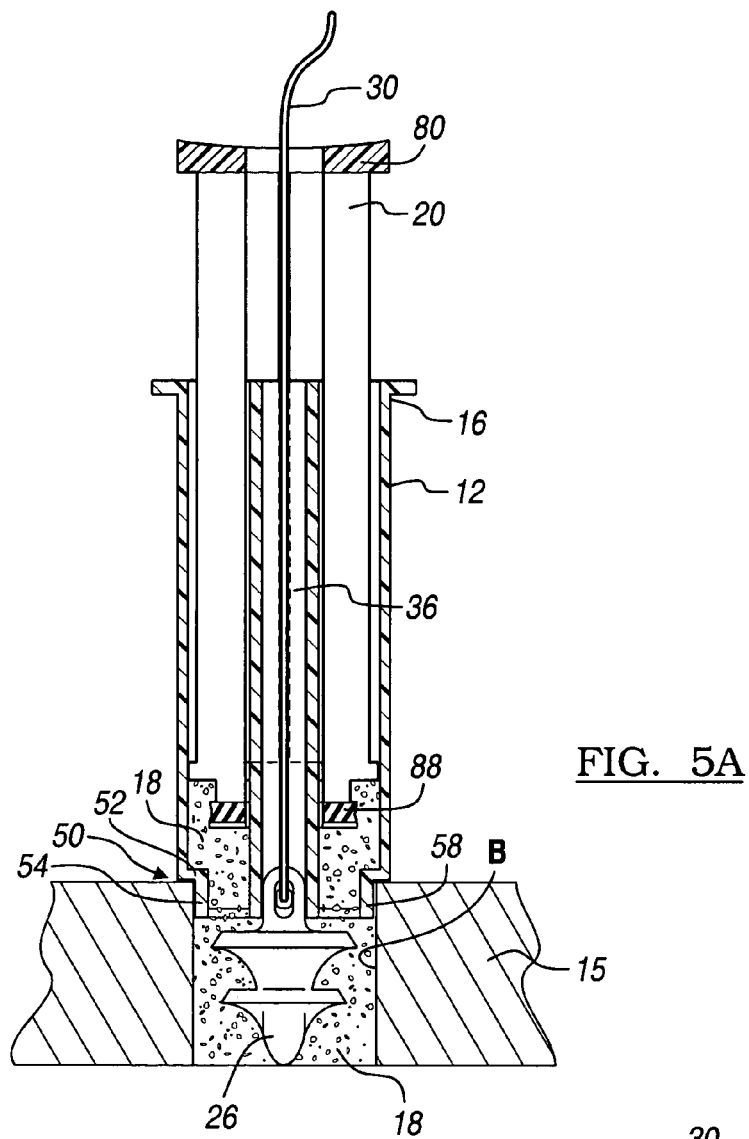
FIG. 5A is a sectional view of the apparatus taken along line 5A-5A of FIG. 2 shown delivering biologic material into a bone hole around a suture anchor.

Referring to the drawings, an apparatus for implanting a suture anchor and delivering biologic material is shown and generally identified at reference 10. The apparatus 10 generally includes a delivery structure 12 having a distal end 14 for locating with a bone hole B of a bone 15 and a proximal end 16 for receiving the biologic material 18 thereat (FIG. 5A). A plunger 20 slidably communicates with the delivery structure 12 to urge the biologic material 18 toward the distal end 14. The delivery structure 12 according to the present teachings is operable to cooperate with an anchor member 26 (FIG. 5A) and suture 30 coupled to and extending from the anchor member 26. Specifically, as will be described in greater detail herein, the delivery structure 12 facilitates injection of the biologic material 18 around the anchor member 26 in the bone hole B while protecting the suture 30 from contact with the biologic material 18 during injection. The biologic material 18 may comprise a biocompatible adhesive or sealant including homopolymers and copolymers of epsilon-caprolactone, lactide, glycolide, para-dioxanone and trimethylene carbonate or other adhesive composition that is biocompatible. The polymers may be blended with synthetic calcium containing bone regenerating materials such as hydroxyapatite, calcium phosphates and bioactive glasses.

The delivery structure 12 generally includes a first or inner longitudinal member 34 defining an inner cavity 36 extending between the distal and proximal ends 14 and 16 and a second or outer longitudinal member 44 disposed around the inner longitudinal member 34 and extending between the distal and proximal ends 14 and 16. The inner and outer longitudinal members 34 and 44 are offset a predetermined distance by supports 46 (best shown in FIG. 3) extending between the inner and outer longitudinal members 34 and 44, respectively.

The inner and outer longitudinal members 34 and 44 define an outer cavity 48 therebetween. The inner and outer longitudinal members 34 and 44 are illustrated as tubular members having circular cross sections and defining an annular space at the outer cavity 48. As such, the detailed discussion herein is directed to longitudinal members defining circular cross sections. It is contemplated, however, that the longitudinal members may comprise any cross sectional shape, such as, but not limited to rectangular and oval.

With particular reference to FIGS. 3-5A, the distal end 14 of the delivery structure 12 provides an annular shoulder portion 50 formed on the outer longitudinal member 44. The shoulder portion 50 defines an annular ledge 52 and a radial wall 54. The shoulder portion 50 provides a relief for the delivery structure 12 to locate properly with respect to the bone hole B during injection of the biologic material 18. The annular space defined between the radial wall 54 and the inner longitudinal member 34 defines an insert portion 58 (FIG. 5A). As will be described, the insert portion 58 is adapted to nest partially into the bone hole B while the shoulder portion 50 rests around the surface surrounding the bone hole B.

An inlet port 60 is incorporated on the outer longitudinal member 44 for delivering the biologic material 18 into the outer cavity 48. The biologic material 18 may be introduced into the outer cavity 48 at the inlet port 60 by a delivery device 64 such as a syringe 66 and plunger 68 assembly. It is appreciated that the biologic material 18 may be introduced into the outer cavity 48 by any other suitable method. For example, the biologic material 18 may be introduced at the opening 70 (FIG. 1) defined between the inner and outer longitudinal members 34 and 44 at the proximal end 16 of the delivery structure 12. In that scenario, the plunger 20 would be withdrawn from the outer cavity 48 to allow the biologic material 18 to be introduced into the outer cavity 48. Once the desired amount of biologic material 18 is introduced into the outer cavity 48, the plunger 20 may be relocated into slidable communication with the delivery structure 12.

Figures 1, 2:
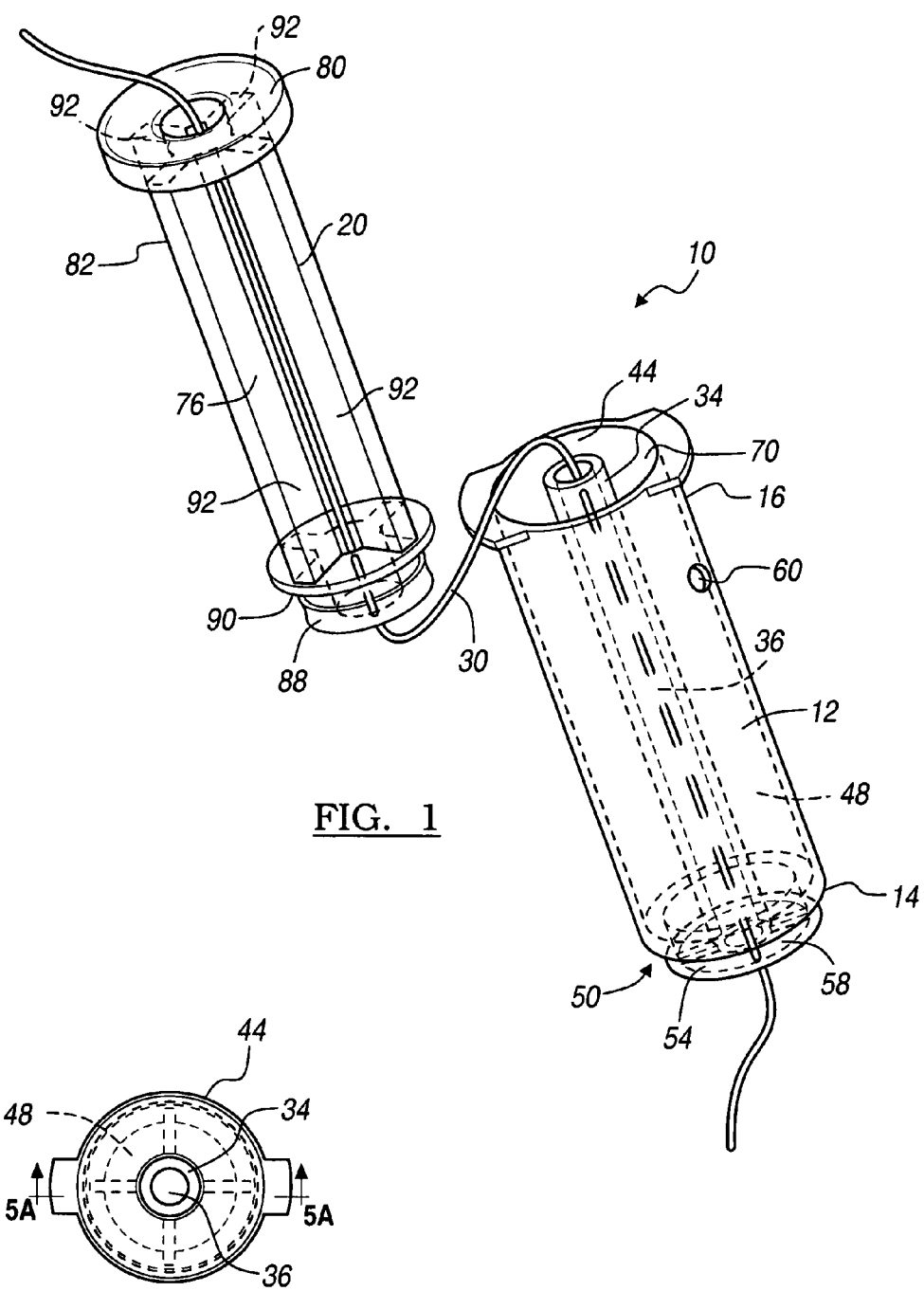
FIG. 1 is a perspective exploded view of the apparatus for implanting a suture anchor and delivering biologic material according to the present teachings.
FIG. 2 is a top view of the apparatus of FIG. 1.
Figure 3:
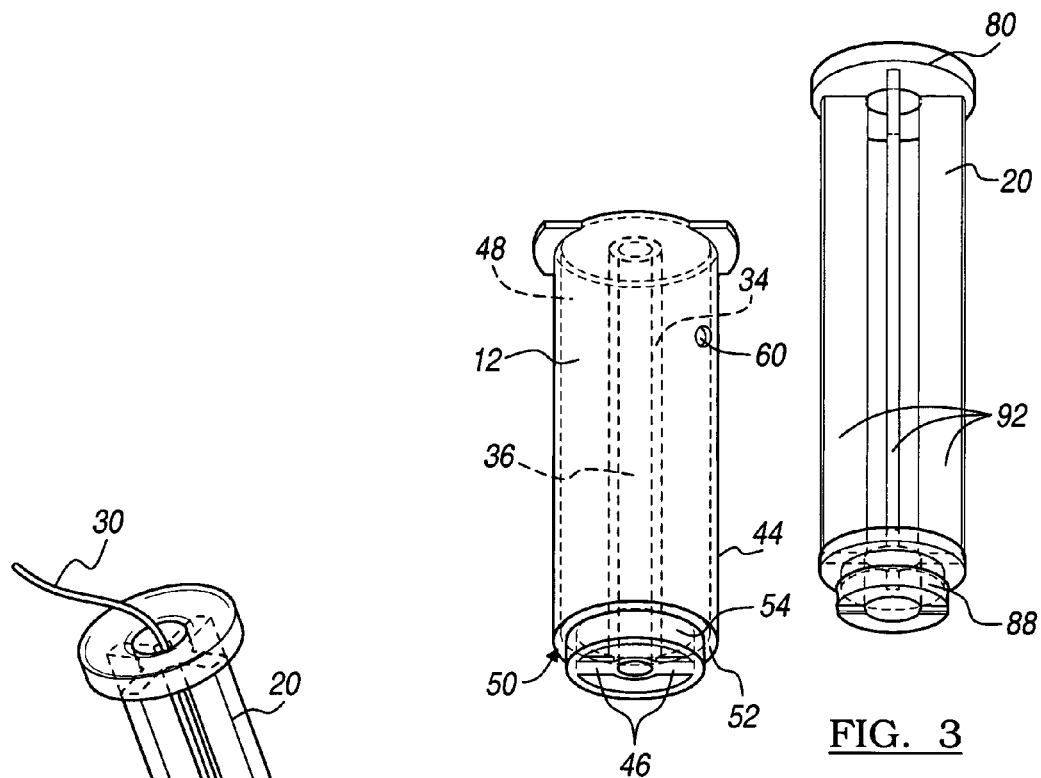
FIG. 3 is a front perspective view of the delivery structure and plunger of FIG. 1.

Turning now to FIGS. 2 and 3, the plunger 20 will be described in greater detail. The plunger 20 generally defines a structure suitable for slidable communication within the outer cavity 48. The plunger 20 includes a main body portion 76, a handle member 80 formed on a proximal end 82 and an engagement portion 88 formed on a distal end 90. The engagement portion 88 defines a geometry suitable for cooperating with the shoulder portion 50 defined by the outer longitudinal member 44. The plunger 20 defines longitudinal wing portions 92 for providing structural support for the delivery structure 12 while slidably communicating with the inner and outer longitudinal members 34 and 44 respectively during operation. It is appreciated that while the plunger 20 is depicted as having four wing portions 92, any number of wing portions 92 may be included.

Figure 4:
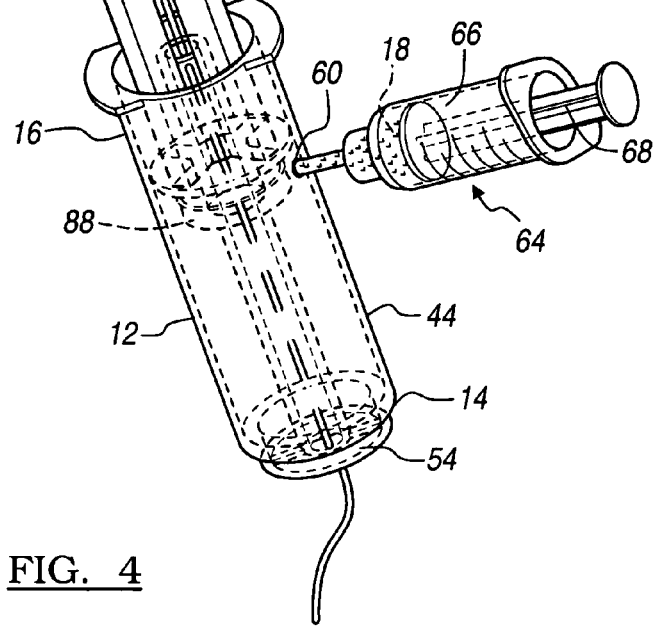
FIG. 4 is a perspective view of the apparatus of FIG. 1 shown cooperating with a delivery device for delivering biologic material to the apparatus.
Figure 5B:
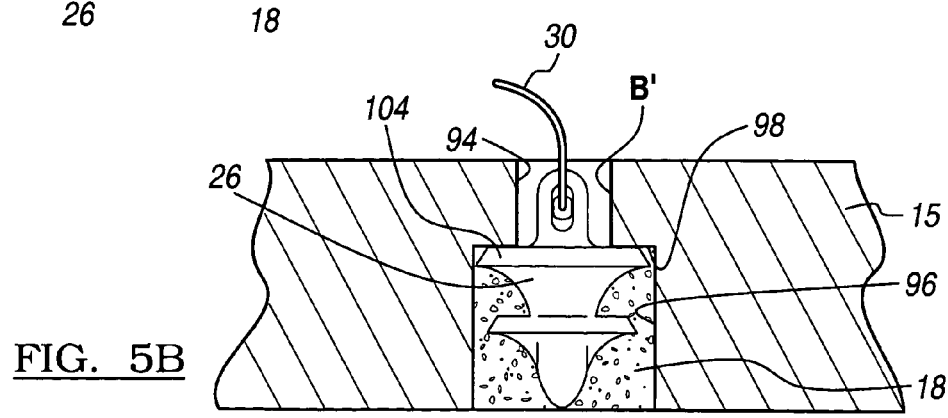
FIG. 5B is a sectional view of an anchor and biologic material delivered to a bone hole according to additional features.

With reference now to FIGS. 4-5B, a method for implanting a suture anchor 26 and biologic material 18 according to the present teachings will be described. At the outset, a bone hole B, FIG. 5A (or B', FIG. 5B) is prepared in the bone 15. As illustrated, a bone hole B having a consistent diameter, or a bone hole B' having a reduced diameter at the bone surface is formed. The bone hole B' illustrated in FIG. 5B defines a first inner diameter 94 and a second inner diameter 96. The first inner diameter 94 presents a radial ledge 98 for providing increased retention properties for the anchor 26 within the bone hole B'. Specifically, an anchor 26 may be selected having ribs 104 extending radially around the anchor 26 a distance defining an outer diameter greater than the inner diameter 94 of the bone hole B'.

Once the bone hole B or B' is prepared, the anchor 26 having a suture 30 extending therefrom is located with respect to the delivery structure 12. In this regard, the suture 30 is passed through the inner cavity 36 of the delivery structure 12 and the anchor 26 is drawn into engagement with the distal end 14 of the delivery structure 12. It is appreciated that while the suture 30 is shown passed through an opening at the proximal end 82 of the plunger 20, the suture 30 may alternately be passed out of the plunger 20 between adjacent wing portions 92 near the distal end 90 of the plunger 20. Next, the distal end 14 of the delivery structure 12 is located relative to the bone hole B or B'. Specifically, the insert portion 58 is located into a nesting relationship with the bone hole B or B' while the shoulder portion 50 supports the delivery structure 12 into a substantially upright, stable position relative to the bone 15.

At this point, the biologic material 18 is introduced into the outer cavity 48 of the delivery structure 12. As previously described, one method for doing so is to inject the biologic material 18 into the outer cavity 48 via the port 60 formed on the outer longitudinal member 44. Once the desired amount of biologic material 18 is injected into the outer cavity 48, the delivery device 64 is removed from engagement with the outer longitudinal member 44. Next, the plunger 20 is slidably actuated toward the bone hole B or B' whereby the biologic material 18 is expelled from the distal end 14 of the delivery structure 12 and into the bone hole B or B' around the anchor 26.

The delivery structure 12 is subsequently removed from the bone hole B or B' allowing the suture 30 to slidably retreat from the inner cavity 36 through the distal end 14 of the delivery structure 12. At this point, the anchor 26 and biologic material 18 are located within the bone hole B or B' and the suture 30, free of biologic material 18, may be used for its desired function.

With reference to FIG. 5B, the anchor 26 is shown in an implanted position with respect to the bone hole B'. It is appreciated that a delivery structure 12 would be provided having an outer diameter compatible with the inner diameter 94 of the bone hole B'. It is also appreciated that the anchor 26 may be implanted into the bone hole B' before utilizing the apparatus 10. In this regard, the suture 30, extending from a pre-installed anchor 26, may be passed through the inner cavity 36 of the delivery structure 12, the delivery structure located for communication with the bone hole B', and biologic material 18 expelled into the bone hole B' around the anchor 26.

While the invention has been described in the specification and illustrated in the drawings with reference to various embodiments, it will be understood by those skilled in the art that various changes may be made and equivalents may be substituted for elements thereof without departing from the scope of the invention as defined in the claims. Furthermore, the mixing and matching of features, elements and/or functions between various embodiments is expressly contemplated herein so that one of ordinary skill in the art would appreciate from this disclosure that features, elements and/or functions of one embodiment may be incorporated into another embodiment as appropriate, unless described otherwise above.

Moreover, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the Forgoing description and the appended claims.

What is claimed is:

1. A method for implanting an anchor and delivering biologic material into a bone hole, the method comprising:
   coupling a flexible member to an anchor;
   positioning the anchor in the bone hole;
   locating a protective barrier relative to said flexible member and in direct contact with said anchor; and
   delivering the biologic material around the bone hole while the anchor is in the bone hole wherein said protective barrier precludes the biologic material from contacting any portion of said flexible member during the delivering of the biologic material.

2. The method of claim 1 wherein locating a protective barrier further comprises:
   locating said flexible member through a first cavity defined by a first longitudinal member; and
   placing the biologic material into a second cavity defined between said first longitudinal member and a second longitudinal member.

3. The method of claim 2 wherein placing the biologic material into the second cavity further comprises:
   injecting the biologic material through a port defined on said second longitudinal member by
   locating a distal tip of a delivery device containing the biologic material at said port; and
   actuating a first plunger slidably disposed within said delivery device whereby the biologic material is transferred from said delivery device to said second cavity.

4. The method of claim 2 wherein delivering the biologic material further comprises:
   actuating a second plunger slidably disposed within said second cavity toward the bone hole whereby the biologic material is forcibly expelled into the bone hole and wherein said second plunger engages said first and second longitudinal members during said actuating.

5. The method of claim 4 wherein actuating said second plunger includes actuating said second plunger along an axis defined by said first longitudinal member.

6. The method of claim 2 wherein positioning the anchor in the bone hole further comprises:
   locating at least a portion of said flexible member out of a proximal end of said first longitudinal member.

7. The method of claim 2 further comprising:
   locating a distal end of said second longitudinal member relative to the bone hole including locating a radially stepped in portion defined at said distal end of said second longitudinal member at least partially into the bone hole.

8. The method of claim 2 further comprising:
   withdrawing the first and second longitudinal members from a location proximate the bone hole whereby said flexible member slidably withdraws from said first cavity.

9. A method for implanting an anchor and delivering biologic material into a bone hole, the method comprising:
   coupling a flexible member to an anchor;
   locating the flexible member through a first cavity defined by a first longitudinal member until the anchor is drawn into direct engagement with the first longitudinal member;
   positioning the anchor in the bone hole; and
   advancing a plunger occupying an annular space between the first longitudinal member and a second longitudinal member disposed around the first longitudinal member, the plunger urging the biologic material from the annular space and into the bone hole around the anchor while the anchor is in the bone hole and the biologic material is precluded from contacting any portion of the flexible member by the first longitudinal member during the plunger advancement.

10. The method of claim 9, further comprising:
    injecting the biologic material through a port defined on the second longitudinal member prior to advancing the plunger.

11. The method of claim 10 wherein injecting the biologic material through the port further comprises:
    locating a distal tip of a delivery device containing the biologic material at the port; and
    actuating a slidable member disposed within the delivery device whereby the biologic material is transferred from the delivery device to the annular space.

12. The method of claim 9 wherein advancing the plunger further comprises:
    engaging the first and second longitudinal members with the plunger during the actuating.

13. The method of claim 12 wherein actuating the plunger includes actuating the plunger along an axis defined by the first longitudinal member.

14. The method of claim 9 wherein positioning the anchor in the bone hole further comprises:
    locating at least a portion of the flexible member out of a proximal end of the first longitudinal member.

15. The method of claim 9 further comprising:
    locating a distal end of the second longitudinal member relative to the bone hole including locating a radially stepped in portion defined at the distal end of the second longitudinal member at least partially into the bone hole.

16. The method of claim 9 further comprising:
    withdrawing the first and second longitudinal members from a location proximate the bone hole whereby the flexible member slidably withdraws from the first cavity.

17. The method of claim 9, further comprising:
    inserting an eyelet of the anchor into the first longitudinal member.

18. The method of claim 9, further comprising:
    forming a stepped bore in the bone; and
    pushing the anchor into the stepped bore.

19. A method for implanting an anchor and delivering biologic material into a bone hole, the method comprising:
    providing a delivery structure defining a proximal end and a distal end and having a first longitudinal member defining a first cavity and extending between the distal and proximal end, a second longitudinal member disposed around the first longitudinal member and extending between the distal and proximal end, the first and second longitudinal members being concentric from the distal end to the proximal end and defining a second cavity therebetween that is concentric with the first cavity;
    passing a suture through the first cavity, the suture being coupled to the anchor;
    engaging the anchor with the distal end of the delivery structure;
    positioning the anchor in the bone hole; and
    advancing a plunger that is disposed within the second cavity to slidably engage the first and second longitudinal members and urge the biologic material from the second cavity into the bone hole around the anchor while the anchor is in the bone hole, the first longitudinal member providing a barrier between the suture and the biologic material from the distal end to the proximal end of the first longitudinal member wherein the first longitudinal member precludes the biologic material from contacting any portion of the suture during the plunger advancement.

20. The method of claim 19 wherein advancing the plunger further comprises advancing the plunger while continuously engaging the first and second longitudinal members through the second cavity between the distal and proximal ends.

21. The method of claim 20, further comprising:
    inserting a portion of the first longitudinal member at least partially into the bone hole during delivery of the biologic material.

22. The method of claim 19 wherein positioning the anchor in the bone hole further comprises:
    positioning the distal end of the delivery structure against the surface of bone that defines the bone hole such that an annular ledge formed on the second longitudinal member locates on the surface of the bone.

23. The method of claim 19, further comprising:
    placing the biologic material into the second cavity.

24. The method of claim 23 wherein placing the biologic material into the second cavity further comprises:
    injecting the biologic material through a port defined on the second longitudinal member.

25. The method of claim 24 wherein injecting the biologic material through the port further comprises:
    locating a distal tip of a delivery device containing the biologic material at the port; and
    actuating a slidable member disposed within the delivery device whereby the biologic material is transferred from the delivery device to the second cavity.

26. The method of claim 23, further comprising:
    withdrawing the first and second longitudinal members from a location proximate the bone hole whereby the suture slidably withdraws from the first cavity.

27. The method of claim 19 wherein engaging the anchor comprises directly engaging the anchor with the distal end of the delivery structure.

* * * * *

UNITED STATES PATENT AND TRADEMARK OFFICE
CERTIFICATE OF CORRECTION

PATENT NO.        : 7,776,041 B1                                     Page 1 of 1
APPLICATION NO.   : 10/889623
DATED             : August 17, 2010
INVENTOR(S)       : Troy M. Walters It is certified that error appears in the above-identified patent and that said Letters Patent is hereby corrected as shown below:

Title Page, item [75], For Inventor, delete "Troy Walters" and insert -- Troy M. Walters --.

Signed and Sealed this
Eighth Day of April, 2014

Michelle K. Lee
*Deputy Director of the United States Patent and Trademark Office*